United States Patent
Inoue et al.

(10) Patent No.: US 7,830,378 B2
(45) Date of Patent: Nov. 9, 2010

(54) MEDICAL IMAGE PROCESSING APPARATUS AND MEDICAL IMAGE PROCESSING METHOD

(75) Inventors: Ryoko Inoue, Hachioji (JP); Hirokazu Nishimura, Hachioji (JP); Hideki Tanaka, Tama (JP); Kenji Nakamura, Chiba (JP); Miho Sawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 46 days.

(21) Appl. No.: 12/238,603

(22) Filed: Sep. 26, 2008

(65) Prior Publication Data
US 2009/0079737 A1 Mar. 26, 2009

Related U.S. Application Data

(63) Continuation of application No. PCT/JP2007/052348, filed on Feb. 9, 2007.

(30) Foreign Application Priority Data

Mar. 28, 2006 (JP) .............................. 2006-089118

(51) Int. Cl.
*G06T 17/00* (2006.01)
(52) U.S. Cl. ....................................................... 345/424
(58) Field of Classification Search .................. None
See application file for complete search history.

(56) References Cited
U.S. PATENT DOCUMENTS
6,016,439 A * 1/2000 Acker ........................ 600/411

6,083,162 A * 7/2000 Vining ........................ 600/407
7,298,879 B2 * 11/2007 Wiemker ..................... 382/128

(Continued)

FOREIGN PATENT DOCUMENTS
JP 11-337845 12/1999

(Continued)

OTHER PUBLICATIONS

Yao, J., Miller, M., Franaszek, M., Summers, R., Colonic Polyp Segmentation in CT Colonography-Based on Fuzzy Clustering and Deformable Models, Nov. 2004, IEEE Transactions on Medical Imaging, vol. 23, No. 11, pp. 1344-1352.*

(Continued)

*Primary Examiner*—Ulka Chauhan
*Assistant Examiner*—Said Broome
(74) *Attorney, Agent, or Firm*—Scully, Scott, Murphy & Presser, P.C.

(57) ABSTRACT

A medical image processing apparatus of the invention comprises: a three-dimensional model estimating section that estimates a three-dimensional model of body tissues based on a two-dimensional image of an image of the body tissues inside a body cavity inputted from a medical image pickup apparatus; a voxel detecting section that detects one voxel existing on a nearest side in a view direction of the medical image pickup apparatus among the voxels included in the three-dimensional model; and a raised shape detecting section that acquires one curved surface including the one voxel to detect a position with gradient variation on the one curved surface and to determine whether or not body tissues with a locally raised shape exist in the position in the three-dimensional model.

12 Claims, 7 Drawing Sheets

U.S. PATENT DOCUMENTS

| | | | |
|---|---|---|---|
| 7,369,638 B2* | 5/2008 | Kiraly et al. ................... | 378/4 |
| 2003/0223627 A1* | 12/2003 | Yoshida et al. .............. | 382/128 |
| 2005/0116957 A1* | 6/2005 | Guang ........................ | 345/501 |
| 2005/0165303 A1 | 7/2005 | Kleen et al. | |
| 2005/0286750 A1* | 12/2005 | Dehmeshki ................ | 382/131 |
| 2006/0221074 A1* | 10/2006 | Matsumoto ................ | 345/424 |

FOREIGN PATENT DOCUMENTS

| | | |
|---|---|---|
| JP | 2005-506140 | 3/2005 |
| JP | 2005-177477 | 7/2005 |
| WO | WO 03/034176 A2 | 4/2003 |

OTHER PUBLICATIONS

Yan-Jun P. et al., "A new tissue segmentation algorithm in 3d data based on boundary model and local character structure" Proceedings SPIE-The International Society for Optical Engineering, 2005, pp. 60441J.1-60441J.6, vol. 6044, Image Analysis Techniques, Hongchao Ma.

* cited by examiner

→ :NORMAL VECTOR

⇢ :REVERSE NORMAL VECTORS

MEDICAL IMAGE PROCESSING APPARATUS AND MEDICAL IMAGE PROCESSING METHOD

CROSS REFERENCE TO RELATED APPLICATION

This application is a continuation application of PCT/JP2007/052348 filed on Feb. 9, 2007 and claims benefit of Japanese Application No. 2006-089118 filed in Japan on Mar. 28, 2006, the entire contents of which are incorporated herein by this reference.

BACKGROUND OF THE INVENTION

1. Field of the Invention

The present invention relates to a medical image processing apparatus and a medical image processing method, and more particularly, to a medical image processing apparatus and a medical image processing method capable of detecting a raised shape in a three-dimensional model of body tissues inside the body cavity.

2. Description of the Related Art

An endoscope system configured by including an endoscope, a medical image processing apparatus, and the like is widely used in the medical field and other fields. Specifically, for example, the endoscope system is configured by including: an endoscope including an insertion portion to be inserted into the body cavity as a living body, an objective optical system arranged at a distal end portion of the insertion portion, and an image pickup section that picks up an image inside the body cavity formed by the objective optical system and outputs the image as an image pickup signal; and a medical image processing apparatus that executes a processing of displaying an image inside the body cavity on a monitor or the like as a displaying section based on the image pickup signal. A user, for example, observes an organ or the like as a subject inside the body cavity based on the image inside the body cavity displayed on the monitor or the like as the displaying section.

Having the above described configuration, the endoscope system can also pick up an image of for example, digestive tract mucosa of large intestine or the like as a subject inside the body cavity. Therefore, the user can comprehensively observe various findings such as color tone of mucosa, shape of lesion, and a fine structure of mucosal surface.

Furthermore, in recent years, an endoscope apparatus such as the one described in Japanese Patent Application Laid-Open Publication No. 11-337845 has been proposed, which is capable of generating a three-dimensional model of a subject based on two-dimensional image data corresponding to an image pickup signal of an image of the subject picked up by the endoscope.

Meanwhile, a method described in US Patent Application Publication No. 2003/0223627 has been proposed as a method for detecting a lesion site such as polyps in a three-dimensional model. The method enables to detect a lesion site in the three-dimensional model by evaluating the shape of the three-dimensional model using a feature value of shape, such as ShapeIndex and Curvedness, on the basis of curvature.

SUMMARY OF THE INVENTION

A first medical image processing apparatus of the present invention comprises: a three-dimensional model estimating section that estimates a three-dimensional model of body tissues based on a two-dimensional image of an image of the body tissues inside a body cavity inputted from a medical image pickup apparatus; a voxel detecting section that detects one voxel existing on a nearest side in a view direction of the medical image pickup apparatus among voxels included in the three-dimensional model; and a raised shape detecting section that acquires one curved surface including the one voxel to detect a position with gradient variation on the one curved surface and to determine whether or not body tissues with a locally raised shape exist in the position in the three-dimensional model.

In a second medical image processing apparatus of the present invention according to the first medical image processing apparatus, the raised shape detecting section traces the one curved surface along a plurality of trace lines set parallel to a predetermined axial direction, and then determines that the body tissues with a locally raised shape exist in one position when detecting that the number of trace lines with intensity gradient variation in the one position in the predetermined axial direction among the plurality of trace lines is equal to or larger than one and equal to or smaller than a predetermined threshold value.

In a third medical image processing apparatus of the present invention according to the second medical image processing apparatus, the predetermined axial direction is a central axis direction of a lumen inside the body cavity.

A fourth medical image processing apparatus of the present invention comprises: an edge extracting section that extracts an edge of a two-dimensional image based on the inputted two-dimensional image of an image of body tissues inside a body cavity; a three-dimensional model estimating section that estimates a three-dimensional model of the body tissues based on the two-dimensional image; a vector calculating section that detects one voxel group including the edge estimated as a part of the three-dimensional model and that calculates a normal vector and a reverse normal vector, which is a vector in which the direction of the normal vector is inverted 180 degrees, in voxels existing at predetermined intervals among the one voxel group; a raised shape determining section that detects a first voxel as a raise start position and a second voxel as a raise end position based on an intersection state of the normal vectors and an intersection state of the reverse normal vectors to thereby determine whether or not the body tissues estimated as the one voxel group are body tissues with a locally raised shape; and a lesion determining section that calculates a distance between the first voxel and the second voxel and determines that the body tissues estimated as the one voxel group are body tissues with a locally raised shape stemmed from a lesion if the distance is equal to or smaller than a predetermined distance.

In a fifth medical image processing apparatus of the present invention according to the fourth medical image processing apparatus, the raised shape determining section sets as the first voxel, a first voxel where normal vectors within a predetermined size of vector start not to intersect each other and the number of intersections of reverse normal vectors within the predetermined size of vector becomes equal to or larger than a first threshold value.

In a sixth medical image processing apparatus of the present invention according to the fifth medical image processing apparatus, the raised shape determining section sets as the second voxel, a first voxel where normal vectors within a predetermined size of vector start to intersect each other and the number of intersections of reverse normal vectors within the predetermined size of vector becomes smaller than a second threshold value.

In a seventh medical image processing apparatus of the present invention according to the sixth medical image processing apparatus, the first threshold value is a value equal to the second threshold value.

A first medical image processing method of the present invention comprises: a three-dimensional model estimating step of estimating a three-dimensional model of body tissues based on a two-dimensional image of an image of the body tissues inside a body cavity inputted from a medical image pickup apparatus; a voxel detecting step of detecting one voxel existing on a nearest side in a view direction of the medical image pickup apparatus among voxels included in the three-dimensional model; and a raised shape detecting step of acquiring one curved surface including the one voxel to detect a position with gradient variation on the one curved surface and to determine whether or not body tissues with a locally raised shape exist in the position in the three-dimensional model.

In the second medical image processing method of the present invention according to the first medical image processing method, the raised shape detecting step is a step of tracing the one curved surface along a plurality of trace lines set parallel to a predetermined axial direction, and then determining that the body tissues with a locally raised shape exist in one position when detecting that the number of trace lines with intensity gradient variation in the one position in the predetermined axial direction among the plurality of trace lines is equal to or larger than one and equal to or smaller than a predetermined threshold value.

In a third medical image processing method of the present invention according to the second medical image processing method, the predetermined axial direction is a central axis direction of a lumen inside the body cavity.

A fourth medical image processing method of the present invention comprises: an edge extracting step of extracting an edge of a two-dimensional image based on the inputted two-dimensional image of an image of body tissues inside a body cavity; a three-dimensional model estimating step of estimating a three-dimensional model of the body tissues based on the two-dimensional image; a vector calculating step of detecting one voxel group including the edge estimated as a part of the three-dimensional model and calculating a normal vector and a reverse normal vector, which is a vector in which the direction of the normal vector is inverted 180°, in voxels existing at predetermined intervals among the one voxel group; a raised shape determining step of detecting a first voxel as a raise start position and a second voxel as a raise end position based on an intersection state of the normal vectors and an intersection state of the reverse normal vectors to thereby determine whether or not the body tissues estimated as the one voxel group are body tissues with a locally raised shape; and a lesion determining step of calculating a distance between the first voxel and the second voxel and determining that the body tissues estimated as the one voxel group are body tissues with a locally raised shape stemmed from a lesion if the distance is equal to or smaller than a predetermined distance.

In a fifth medical image processing method of the present invention according to the fourth medical image processing method, the raised shape determining step is a step of setting as the first voxel, a first voxel where normal vectors within a predetermined size of vector start not to intersect each other and the number of intersections of reverse normal vectors within the predetermined size of vector becomes equal to or larger than a first threshold value.

In a sixth medical image processing method of the present invention according to the fifth medical image processing method, the raised shape determining step is a step of setting as the second voxel, a first voxel where normal vectors within a predetermined size of vector start to intersect each other and the number of intersections of reverse normal vectors within the predetermined size of vector becomes smaller than a second threshold value.

In a seventh medical image processing method of the present invention according to the sixth medical image processing method, the first threshold value is a value equal to the second threshold value.

DESCRIPTION OF THE PREFERRED EMBODIMENT(S)

Embodiments of the present invention will now be described with reference to the drawings.

First Embodiment

Figure 1:
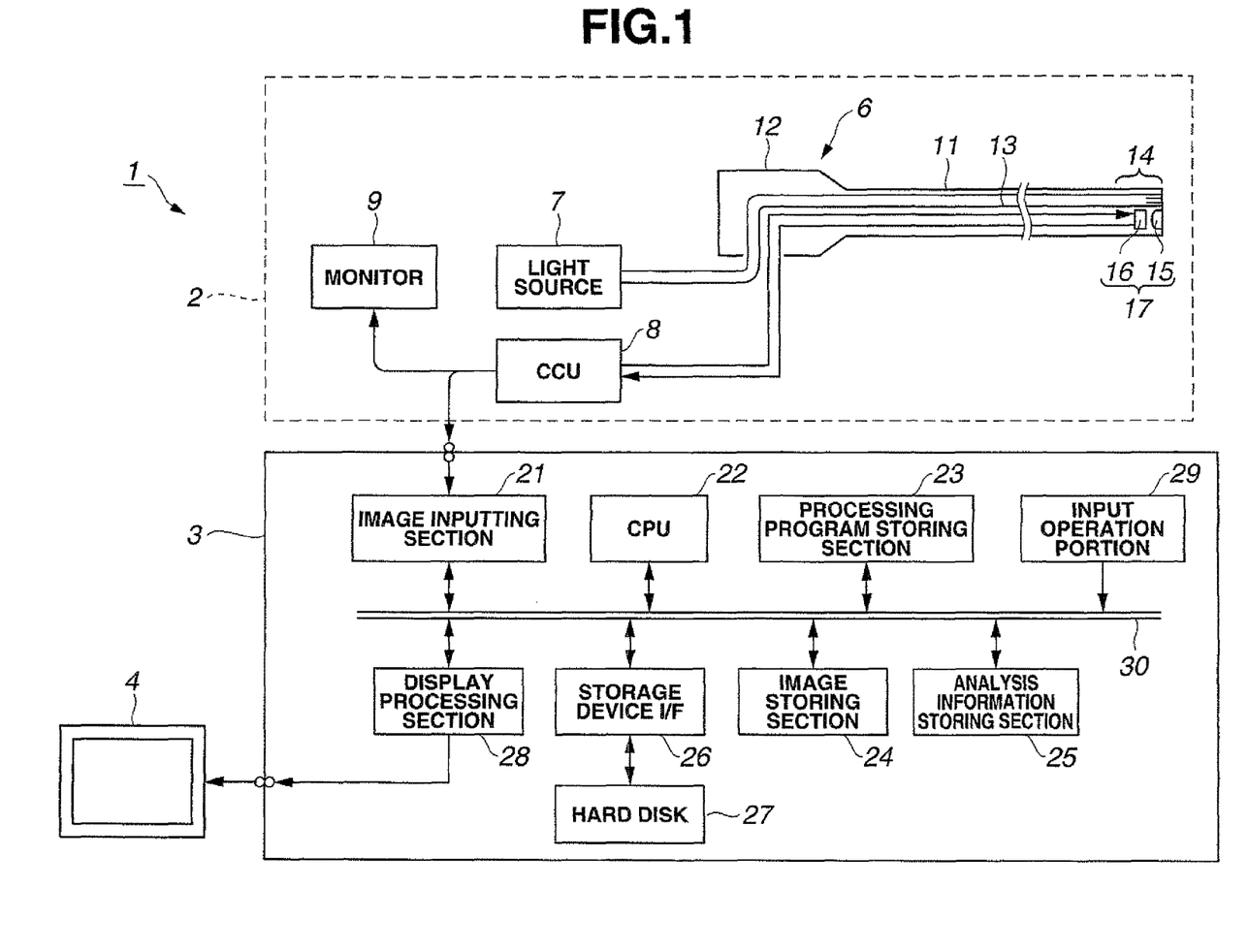
FIG. 1 is a diagram showing an example of an overall configuration of an endoscope system in which a medical image processing apparatus according to an embodiment of the present invention is used.
Figure 2:
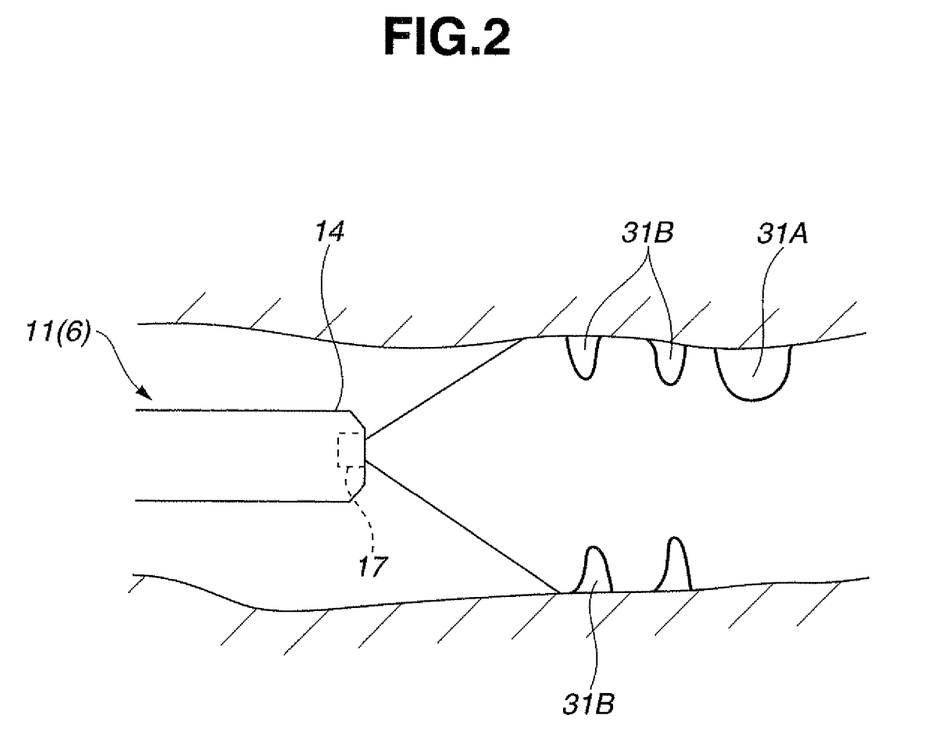
FIG. 2 is a schematic diagram showing a state when the endoscope of FIG. 1 is inserted into a tubular organ.
Figure 3:
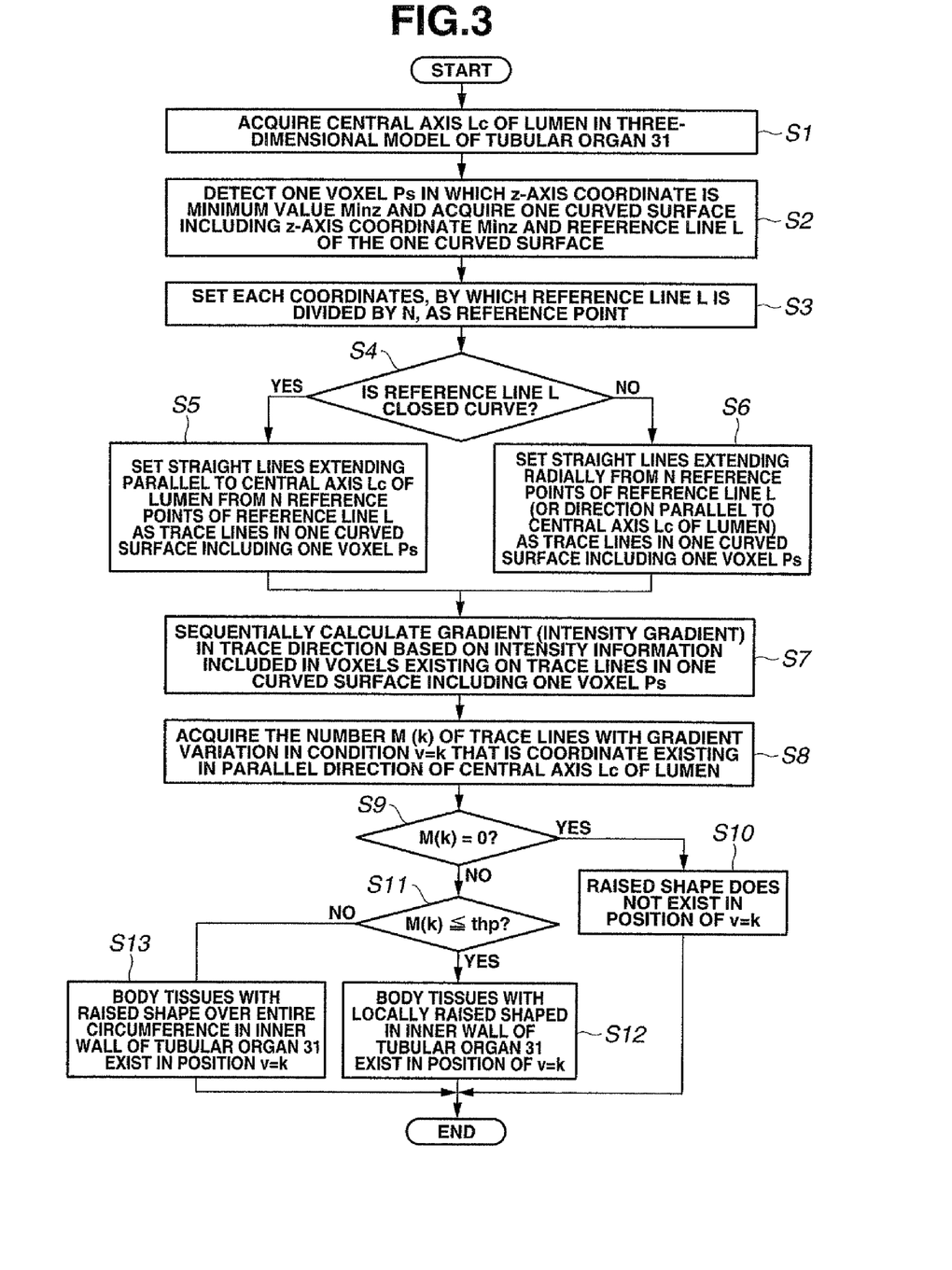
FIG. 3 is a flow chart showing a procedure of a processing executed by the medical image processing apparatus of FIG. 1 in a first embodiment.
Figure 4:
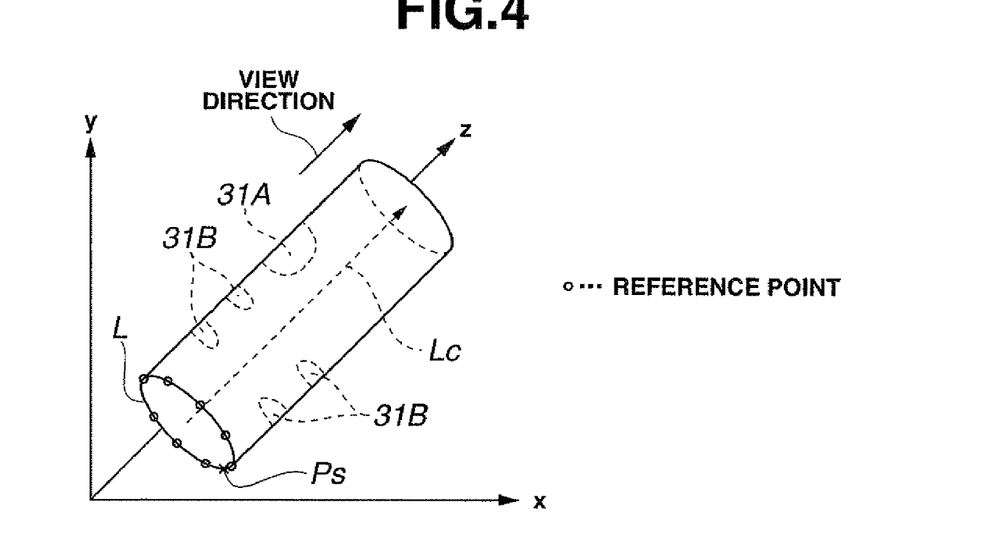
FIG. 4 is a diagram showing an example of a three-dimensional model of body tissues estimated by the medical image processing apparatus of FIG. 1.
Figure 5:
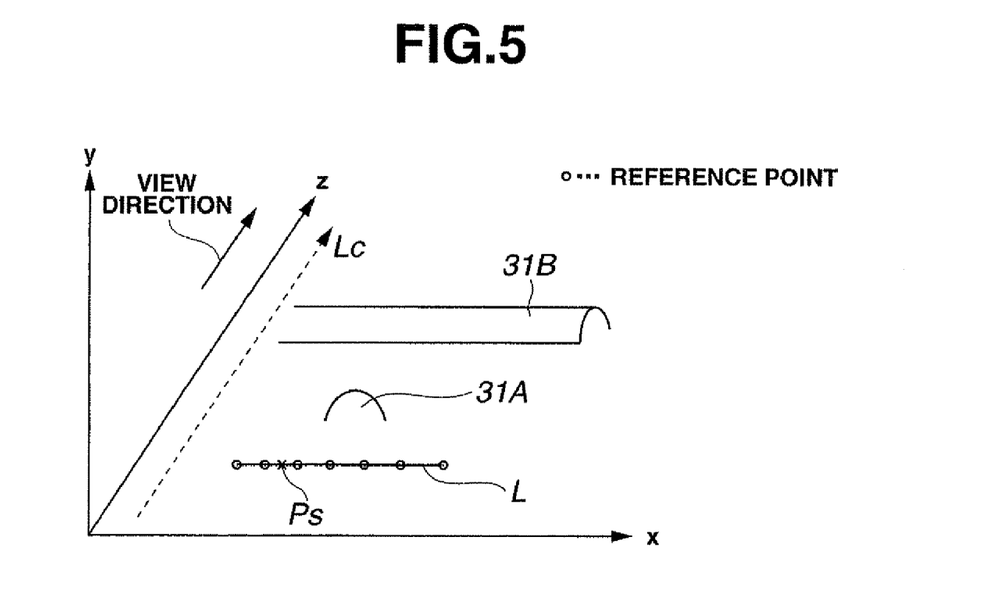
FIG. 5 is a diagram showing an example, different from FIG. 4, of a three-dimensional model of body tissues estimated by the medical image processing apparatus of FIG. 1.
Figure 6:
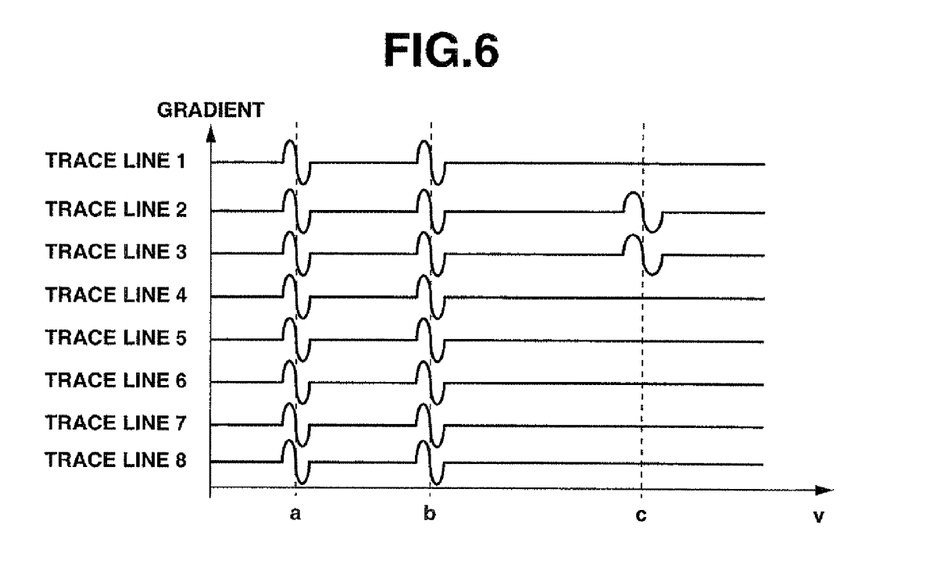
FIG. 6 is a diagram showing variations in gradient of trace lines in the three-dimensional model of FIG. 4.
Figure 7:
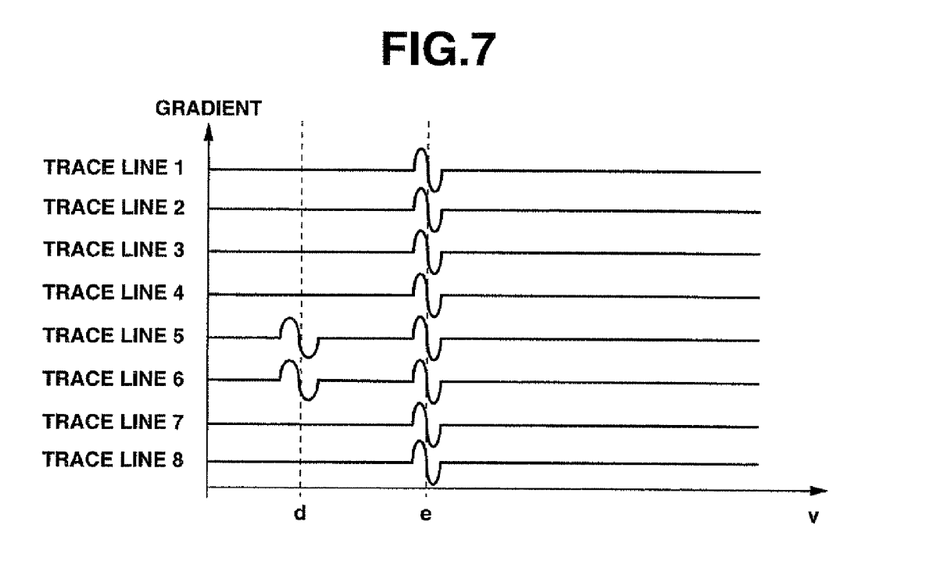
FIG. 7 is a diagram showing variations in gradient of trace lines in the three-dimensional model of FIG. 5.

FIGS. 1 to 7 relate to a first embodiment of the present invention. FIG. 1 is a diagram showing an example of an overall configuration of an endoscope system in which a medical image processing apparatus according to the embodiment of the present invention is used. FIG. 2 is a schematic diagram showing a state when the endoscope of FIG. 1 is inserted into a tubular organ. FIG. 3 is a flow chart showing a procedure of a processing executed by the medical image processing apparatus of FIG. 1 in the first embodiment. FIG. 4 is a diagram showing an example of a three-dimensional model of body tissues estimated by the medical image processing apparatus of FIG. 1. FIG. 5 is a diagram showing an example, different from FIG. 4, of a three-dimensional model of body tissues estimated by the medical image processing apparatus of FIG. 1. FIG. 6 is a diagram showing variations in gradient of trace lines in the three-dimensional model of FIG. 4. FIG. 7 is a diagram showing variations in gradient of trace lines in the three-dimensional model of FIG. 5.

As shown in FIG. 1, main parts of an endoscope system 1 are configured by including: a medical observation apparatus 2 that picks up an image of a subject and outputs a two-dimensional image of the image of the subject; a medical image processing apparatus 3 that applies image processing to a video signal of the two-dimensional image outputted from the medical observation apparatus 2 and outputs the video signal applied with the image processing as an image signal, the medical image processing apparatus 3 being configured by a personal computer and the like; and a monitor 4 that displays an image based on the image signal outputted from the medical image processing apparatus 3.

Main parts of the medical observation apparatus 2 are configured by including: an endoscope 6 that is inserted inside a body cavity and picks up an image of a subject inside the body cavity to output the image as an image pickup signal; a light source 7 that supplies illumination light for illuminating the subject picked up by the endoscope 6; a camera control unit (hereinafter abbreviated as CCU) 8 that applies various controls to the endoscope 6 and applies signal processing to the image pickup signal outputted from the endoscope 6 to output the signal as a video signal of the two-dimensional image; and a monitor 9 for displaying an image of the subject picked up by the endoscope 6 based on the video signal of the two-dimensional image outputted from the CCU 8.

The endoscope 6 is configured by including an insertion portion 11 to be inserted inside the body cavity and an operation portion 12 arranged at a proximal end side of the insertion portion 11. A light guide 13 for transmitting illumination light supplied from the light source 7 is inserted from the proximal end side in the insertion portion 11 into a distal end portion 14 of a distal end side in the insertion portion 11.

The distal end side of the light guide 13 is arranged at the distal end portion 14 of the endoscope 6, and the posterior end side is connected to the light source 7. With such a configuration, the light guide 13 transmits illumination light supplied from the light source 7, and the illumination light is emitted from an illumination window not shown arranged on a distal end surface of the distal end portion 14 of the insertion portion 11. The illumination light is emitted from the illumination window not shown to illuminate body tissues or the like as a subject.

An image pickup section 17 including an objective optical system 15 attached to an observation widow not shown adjacent to the illumination window not shown and an image pickup device 16 that is arranged at the image-forming position of the objective optical system 15 and that is configured by a CCD (charge coupled device) and the like is installed on the distal end portion 14 of the endoscope 6. With such a configuration, the image of a subject formed by the objective optical system 15 is picked up by the image pickup device 16 and thereafter outputted as an image pickup signal.

The image pickup device 16 is connected to the CCU 8 through a signal line. The image pickup device 16 is driven based on a drive signal outputted from the CCU 8 and outputs an image pickup signal to the CCU 8.

Signal processing is applied to the image pickup signal inputted to the CCU 8 by a signal processing circuit not shown arranged inside the CCU 8, and the image pickup signal is converted and outputted as a video signal of the two-dimensional image. The video signal of the two-dimensional image outputted from the CCU 8 is outputted to the monitor 9 and the medical image processing apparatus 3. In this way, an image of the subject based on the image pickup signal outputted from the CCU 8 is displayed as a two-dimensional image on the monitor 9.

The medical image processing apparatus 3 includes an image inputting section 21 that applies A/D conversion to the video signal of the two-dimensional image outputted from the medical observation apparatus 2 and that outputs the video signal, a CPU 22 as a central processing unit that applies image processing to the video signal outputted from the image inputting section 21, a processing program storing section 23 in which a processing program related to the image processing is written, an image storing section 24 that stores the video signal and the like outputted from the image inputting section 21, and an information storing section 25 that stores image data and the like as an image processing result of the CPU 22.

The medical image processing apparatus 3 includes a storage device interface 26, a hard disk 27 as a storage device that stores image data and the like as image processing results of the CPU 22 through the storage device interface 26, a display processing section 28 that executes display processing for displaying the image date on the monitor 4 based on the image data as an image processing result of the CPU 22 and that outputs the image data applied with the display processing as an image signal, and an input operation portion 29 configured by a keyboard or the like allowing a user to input parameters for image processing performed by the CPU 22 and an operation instruction to the medical image processing apparatus 3. The monitor 4 displays an image based on the image signal outputted from the display processing section 28.

Note that, the image inputting section 21, the CPU 22, the processing program storing section 23, the image storing section 24, the information storing section 25, the storage device interface 26, the display processing section 28, and the input operation portion 29 of the medical image processing apparatus 3 are interconnected through a data bus 30.

An operation of the endoscope system 1 will now be described.

As shown in FIG. 2, a user first inserts the insertion portion 11 of the endoscope 6 into, for example, a tubular organ 31 such as large intestine. When the user inserts the insertion portion 11 into the tubular organ 31, the image pickup section 17 arranged at the distal end portion 14 picks up an image of, for example, body tissues 31A and 31B existing on the inner wall of the tubular organ 31. The image of the body tissues 31A and 31B picked up by the image pickup section 17 is outputted to the CCU 8 as an image pickup signal.

A signal processing circuit not shown of the CCU 8 applies signal processing to the image pickup signal outputted from the image pickup device 16 of the image pickup section 17 to thereby covert and output the image pickup signal as a video signal of the two-dimensional image. The monitor 9 displays the image of the body tissues 31A and 31B as a two-dimensional image based on the video signal outputted from the CCU 8. The CCU 8 outputs the video signal of the two-dimensional image obtained by applying signal processing to the image pickup signal outputted from the image pickup device 16 of the image pickup section 17 to the medical image processing apparatus 3.

The image inputting section 21 applies A/D conversion to the video signal of the two-dimensional image outputted to the medical image processing apparatus 3, and the video signal applied with A/D conversion is inputted to the CPU 22.

The CPU 22 as a three-dimensional model estimation section executes processings such as geometrical transformation or the like to estimate a three-dimensional model of the tubular organ 31 including the body tissues 31A and 31B based on intensity information and the like of the video signal of the two-dimensional image outputted from the image inputting section 21.

The CPU 22 further executes processings described below based on the three-dimensional model of the tubular organ 31 including the body tissues 31A and 31B to detect raised shapes of the body tissues 31A and 31B and to determine what kind of body tissues form the detected raised shapes.

The CPU 22 first acquires a central axis Lc of a lumen in the three-dimensional model of the tubular organ 31 based on the estimated three-dimensional model (step S1 of FIG. 3).

Next, the CPU 22 as a voxel detecting section and a raised shape detecting section detects one voxel Ps that is one voxel existing on the nearest side in the view direction of the endoscope 6 among the voxels existing in the estimated three-dimensional model and in which a z-axis coordinate as an axis substantially parallel to the view direction of the endoscope 6 is a minimum value Minz and acquires one curved surface with the z-axis coordinate Minz included in the one voxel Ps and a reference line L of the one curved surface (step S2 of FIG. 3).

Subsequently, the CPU 22 sets each of N coordinates, by the reference line L is divided by N, as a reference point (step S3 of FIG. 3) and determines whether the acquired reference line L is a closed curve.

If the acquired reference line L is a closed curve (step S4 of FIG. 3), the CPU 22, for example, sets straight lines parallel to the central axis Lc of the lumen from the set N reference points of the reference line L set as shown in FIG. 4 as trace lines in one curved surface including one voxel Ps (step S5 of FIG. 3).

If the acquired reference line L is not a closed curve (step S4 of FIG. 3), the CPU 22, for example, sets straight lines extending radially (or parallel to the central axis Lc of the lumen) from the set N reference points of the reference line L set as shown in FIG. 5 as trace lines in one curved surface including one voxel Ps (step S6 of FIG. 3).

The CPU 22 as a raised shape detecting section traces the voxels existing on the trace lines in the one curved surface including the one voxel Ps based on the trace lines set by executing the processing of step S5 or step S6 of FIG. 3 and sequentially calculates the gradient (intensity gradient) in the trace direction based on intensity information included in the voxels (step S7 of FIG. 3).

When the central axis Lc of the lumen is defined as v-axis, the CPU 22 acquires the number $M(k)$ (integer value, where $0 \leq M(k) \leq N$) of trace lines with gradient variation in condition $v=k$ that is a coordinate in the central axis Lc direction of the lumen (step S8 of FIG. 3). In other words, executing such a processing, the CPU 22 detects a position with gradient variation in the one curved surface including the one voxel Ps.

For example, if a trace line is set to each of eight reference points as shown in FIG. 4 (N=8 in FIG. 4) and the trace direction is from the near side to the far side in the view direction, the CPU 22 detects the gradient variations in the v-axis direction of the trace lines in the one curved surface including the one voxel Ps as variations shown in FIG. 6. In a different example, if a trace line is set to each of the eight reference points as shown in FIG. 5 (N=8 in FIG. 5) and the trace direction is from the near side to the far side in the view direction, the CPU 22 detects the gradient variations in the v-axis direction of the trace lines in the one curved surface including the one voxel Ps as variations shown in FIG. 7.

The CPU 22 determines that a raised shape does not exist in a position of $v=k$ where the value of $M(k)$ is 0 (steps S9 and S10 of FIG. 3).

The CPU 22 further compares the value of $M(k)$ with a threshold value thp in each position of $v=k$ where the value of $M(k)$ is one or greater (steps S9 and S11 of FIG. 3).

Subsequently, when the CPU 22 as a raised shape detecting section detects that the value of $M(k)$ is equal to or smaller than the threshold value thp (step S11 of FIG. 3), the CPU 22 determines that a lesion site as body tissues with a locally raised shape in the inner wall of the tubular organ 31 exists in a position of $v=k$ where the value of $M(k)$ is provided (step S12 of FIG. 3).

Specifically describing in other words using FIGS. 4 and 6 as an example, the CPU 22 determines that a lesion site as body tissues with a locally raised shape in the inner wall of the tubular organ 31 such as the body tissues 31A shown in FIG. 4 exists in a position of $v=c$ where $M(c)=2$. Specifically describing in other words using FIGS. 5 and 7 as a different example, the CPU 22 determines that a lesion site as body tissues with a locally raised shape in the inner wall of the tubular organ 31 such as the body tissues 31A shown in FIG. 5 exists in a position of $v=d$ where $M(d)=2$.

When the CPU 22 detects that the value of $M(k)$ is larger than the threshold thp (step S11 of FIG. 3), the CPU 22 determines that folds of large intestine or the like as body tissues including a raised shape over the entire circumference in the inner wall of the tubular organ 31 exist in a position of $v=k$ where the value of $M(k)$ is provided (step S13 of FIG. 3).

Specifically describing in other words using FIGS. 4 and 6 as an example, the CPU 22 determines that folds of large intestine or the like as body tissues including a raised shape over the entire circumference of the inner wall of the tubular organ 31 such as the body tissues 31B shown in FIG. 4 exist in positions of $v=a$ where $M(a)=8$ and $v=b$ where $M(b)=8$. Specifically describing in other words using FIGS. 5 and 7 as a different example, the CPU 22 determines that folds of large intestine or the like as body tissues including a raised shape over the entire circumference of the inner wall of the tubular organ 31 such as the body tissues 31B shown in FIG. 5 exist in a position of $v=e$ where $M(e)=8$.

In addition to the processings described above, the CPU 22 controls the display processing section 28 to superimpose character strings, color, or the like, for illustrating a position where body tissues, such as the body tissues 31A shown in FIG. 4 or 5, with a locally raised shape in the inner wall of the tubular organ 31 exist, on the three-dimensional model. In this way, the monitor 4 displays an image of a three-dimensional model of the tubular organ 31 that can be easily discovered by the user and that includes the body tissues 31A and 31B without confusing a lesion site as body tissues with a locally raised shape in the inner wall of the tubular organ 31 such as the body tissues 31A with the folds of large intestine or the like as body tissues with a raised shape over the entire circumference of the inner wall of the tubular organ 31 such as the body tissues 31B.

The CPU 22 may be designed to detect the pixels on the two-dimensional image existing in positions corresponding to the positions of the voxels based on the positions of the voxels in which body tissues with a locally raised shape are determined to exist. The CPU 22 may also be designed to control the display processing section 28 to superimpose character strings, colors, or the like, for illustrating that the body tissues 31C form a raised shape, on the two-dimensional images including the pixels.

The medical image processing apparatus 3 of the present embodiment executes a series of the above described processings, thereby enabling to prevent overlooking of a lesion site such as polyps and reducing the burden of the user when the user uses a three-dimensional model to observe a subject.

Second Embodiment

Figure 8:
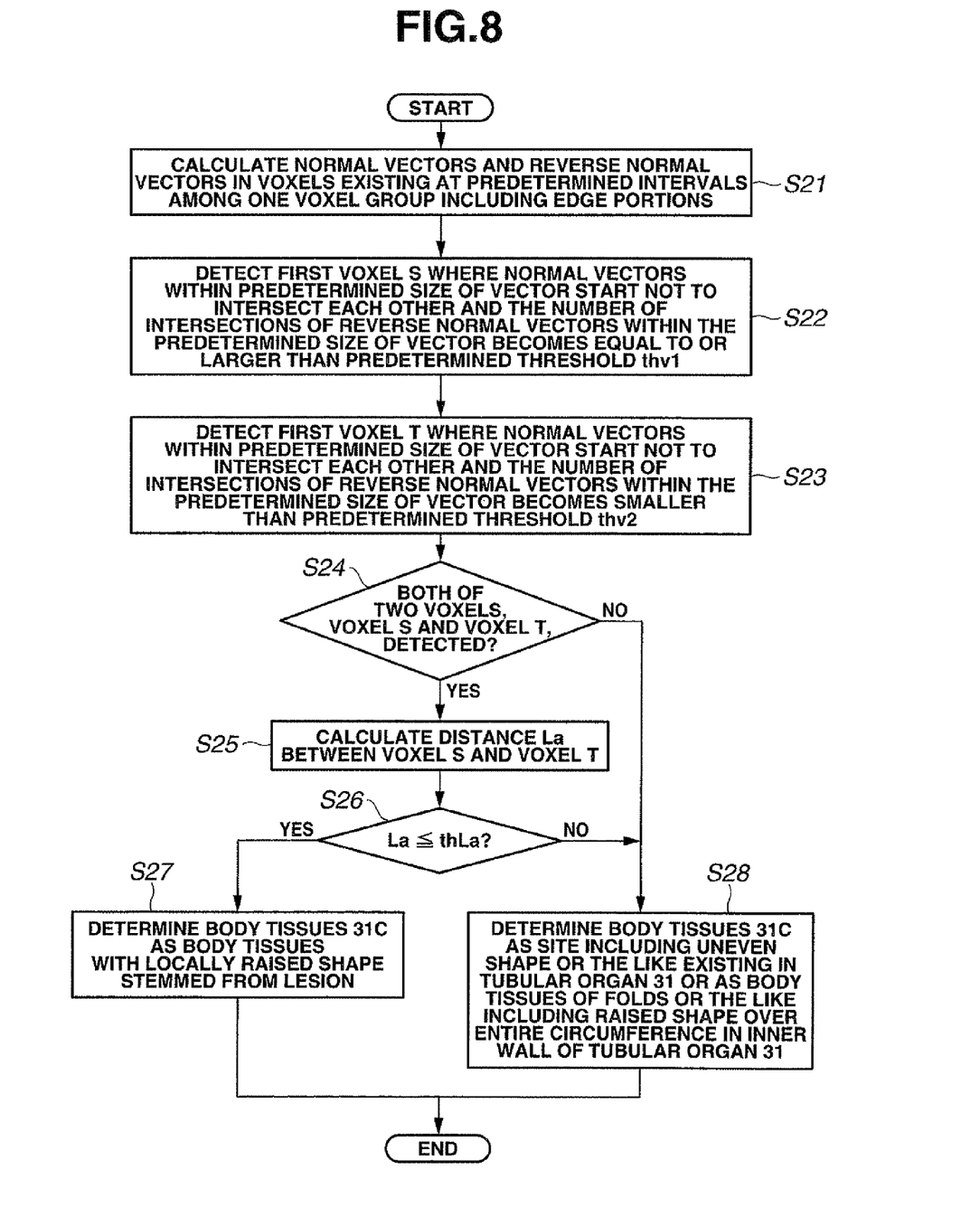
FIG. 8 is a flow chart showing a procedure of a processing executed by the medical image processing apparatus of FIG. 1 in a second embodiment.
Figure 9:
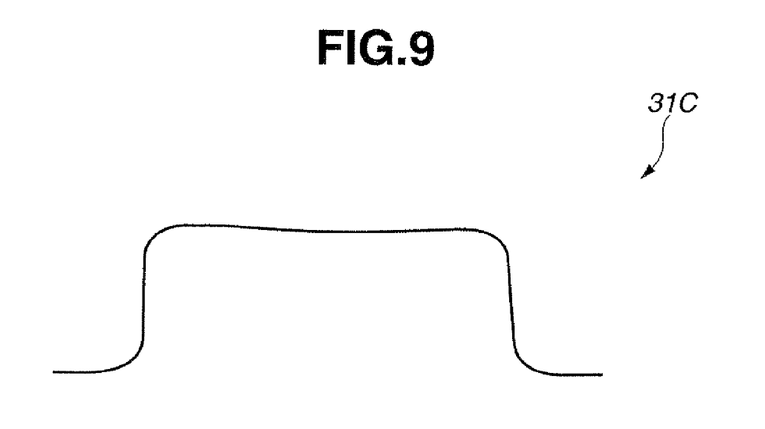
FIG. 9 is a cross-sectional view of a three-dimensional model of one set of body tissues estimated by the medical image processing apparatus of FIG. 1, the three-dimensional model being in a schematic form.
Figure 10:
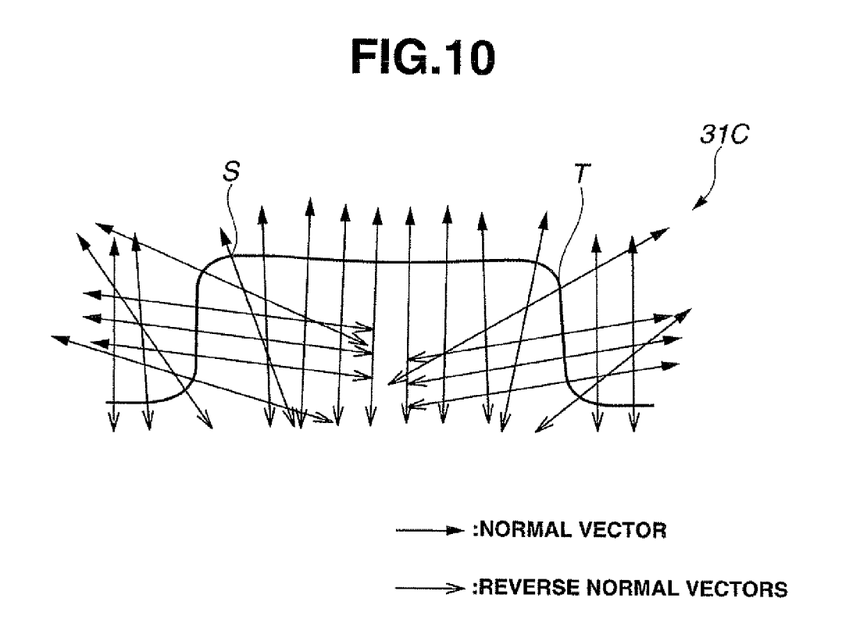
FIG. 10 is a diagram showing normal vectors and reverse normal vectors in FIG. 9.

FIGS. 8 to 10 relate to a second embodiment of the present invention. The detailed description of the parts with similar configurations as in the first embodiment will be omitted. The same reference numerals are used for similar constituent elements as in the first embodiment, and the description thereof will be omitted. The configuration of the endoscope system 1 used in the present embodiment is similar to the one in the first embodiment.

FIG. 8 is a flow chart showing a procedure of processings executed by the medical image processing apparatus of FIG. 1 in the second embodiment. FIG. 9 is a cross-sectional view of a three-dimensional model of one set of body tissues estimated by the medical image processing apparatus of FIG. 1, the three-dimensional model being in a schematic form. FIG. 10 is a diagram showing normal vectors and reverse normal vectors in FIG. 9.

Based on a video signal of a two-dimensional image that is outputted from the image inputting section 21 and in which an image of the tubular organ 31 is picked up, the CPU 22 as an edge extracting section applies, for example, a bandpass filter to the red component of the two-dimensional image to extract all edge portions included in the two-dimensional image. The CPU 22 temporarily stores edge information, which is information related to the positions of pixel groups in which the edge portions are extracted, in the information storing section 25.

The CPU 22 as a three-dimensional model estimating section executes a processing such as geometrical transformation to estimate the three-dimensional model of the tubular organ 31 based on intensity information or the like of a video signal of a two-dimensional image outputted from the image inputting section 21 and to detect one voxel group including edge portions in the three-dimensional model based on the edge information stored in the information storing section 25. The CPU 22 further applies the following processings to the one voxel group to determine whether one set of body tissues formed into a three-dimensional model by the one voxel group includes a raised shape stemmed from a lesion.

First, the CPU 22 as a vector calculating section detects one voxel group including edge portions in the three-dimensional model of the tubular organ 31 and calculates normal vectors and reverse normal vectors in which the directions of the normal vectors are inverted 180°, in the voxels existing at predetermined intervals among the voxel group (step S21 of FIG. 8). More specifically, for example, if a three-dimensional model of body tissues 31C including a cross-sectional shape as shown in FIG. 9 is detected, normal vectors and reverse normal vectors are calculated in the voxels existing at predetermined intervals as shown in FIG. 10.

Next, the CPU 22 as a raised shape determining section detects, for example, a voxel S shown in FIG. 10 as a first voxel, which serves as a raise start position, where the normal vectors within a predetermined size of vector start not to intersect each other and the number of intersections of the reverse normal vectors within the predetermined size of vector becomes equal to or larger than a threshold value thv1, based on the normal vectors and the reverse normal vectors included in the voxels (step S22 of FIG. 8). The CPU 22 as a raised shape determining section further detects, for example, a voxel T shown in FIG. 10 as a first voxel, which serves as a raise end position, where the normal vectors within a predetermined size of vector start to intersect each other and the number of intersections of the reverse normal vectors within the predetermined size of vector becomes smaller than a threshold value thv2, based on the normal vectors and the reverse normal vectors included in the voxels (step S23 of FIG. 8).

Note that, in the present embodiment, the threshold value thv1 and the threshold value thv2 may be different values or the same values.

Subsequently, the CPU 22 as a raised shape determining section determines whether two voxels, the voxel S and the voxel T, have been detected in the three-dimensional model of the body tissues 31C. If both of the two voxels, the voxel S and the voxel T, have been detected (step S24 of FIG. 8), the CPU 22 further calculates a distance La between the voxel S and voxel T (step S25 of FIG. 8). If one or both of the two voxels, the voxel S and the voxel T, have not been detected (step S24 of FIG. 8), the CPU 22 determines the body tissues 31C formed into a three-dimensional model as one voxel group including edge portions as, for example, a site including an uneven shape or the like existing in the tubular organ 31 or as body tissues of folds or the like including a raised shape over the entire circumference in the inner wall of the tubular organ 31, not as body tissues with a locally raised shape stemmed from a lesion (step S28 of FIG. 8). The CPU 22 then ends the series of processings.

The CPU 22 as a lesion determining section further compares the calculated distance La between the voxel S and the voxel T with a threshold value thLa. When detecting that the distance La between the voxel S and the voxel T is equal to or smaller than the threshold value thLa, the CPU 22 as the lesion determining section determines the body tissues 31C formed into a three-dimensional model as one voxel group including edge portions, as body tissues with a locally raised shape stemmed from a lesion (step S27 of FIG. 8). The CPU 22 then ends the series of processings. When detecting that the distance La between the voxel S and the voxel T is larger than the threshold value thLa, the CPU 22 determines the body tissues 31C formed into a three-dimensional model as one voxel group including edge portions as, for example, a site including an uneven shape or the like existing in the tubular organ 31 or as body tissues of folds or the like including a raised shape over the entire circumference in the inner wall of the tubular organ 31, not as body tissues with a locally raised shape stemmed from a lesion (step S28 of FIG. 8). The CPU 22 then ends the series of processings.

In addition to the processings described above, the CPU 22 controls the display processing section 28 to superimpose character strings, color, or the like, for illustrating a position where body tissues 31C with a raised shape stemmed from a lesion exist, on the three-dimensional model. In this way, the monitor 4 displays an image of a three-dimensional model of the tubular organ 31 that can be easily discovered by the user and that includes the body tissues 31C without confusing the raised shape stemmed from a lesion with the site including an uneven shape or body tissues such as folds and the like.

The CPU 22 may be designed to detect the pixels on the two-dimensional image existing in positions corresponding to the positions of the voxels based on the positions of the voxels in which body tissues with a locally raised shape are determined to exist. The CPU 22 may also be designed to control the display processing section 28 to superimpose character strings, colors, and the like, for illustrating that the body tissues 31A form a raised shape, on two-dimensional images including the pixels.

The medical image processing apparatus 3 of the present embodiment executes a series of the above described processings, thereby enabling to prevent overlooking of a lesion site such as polyps and reducing the burden of the user when the user uses a three-dimensional model to observe a subject.

Note that, the series of processings executed by the CPU 22 in the present embodiment are not limited to the processings applied to the three-dimensional model of the tubular organ 31. The processings may also be applied to, for example, a two-dimensional image of the tubular organ 31.

It is obvious that the present invention is not limited to the embodiments described above, but is capable of various modifications and applications without departing from the scope of the invention.

What is claimed is:

1. A medical image processing apparatus comprising:
   an image storage that stores a two-dimensional image of an image of body tissues inside a body cavity inputted from a medical image pickup apparatus;
   a three-dimensional model estimating section that estimates a three-dimensional model of body tissues based on the two-dimensional image of the image of the body tissues inside the body cavity inputted from the medical image pickup apparatus;
   a voxel detecting section that detects one voxel existing on a nearest side in a view direction of the medical image pickup apparatus among voxels included in the three-dimensional model;
   a raised shape detecting section that acquires one curved surface including the one voxel to detect a position with gradient variation on the one curved surface and to determine whether or not body tissues with a locally raised shape exist in the position in the three-dimensional model; and
   the raised shape detecting section traces the one curved surface along a plurality of trace lines set parallel to a predetermined axial direction, and then determines that the body tissues with a locally raised shape exist in one position when detecting that the number of trace lines with intensity gradient variation in the one position in the predetermined axial direction among the plurality of trace lines is equal to or larger than one and equal to or smaller than a predetermined threshold value.

2. The medical image processing apparatus according to claim 1, wherein
   the predetermined axial direction is a central axis direction of a lumen inside the body cavity.

3. A medical image processing apparatus comprising:
   an image storage that stores a two-dimensional image of an image of body tissues inside a body cavity inputted from a medical image pickup apparatus;
   an edge extracting section that extracts an edge of the two-dimensional image based on the inputted two-dimensional image of the image of body tissues inside the body cavity;
   a three-dimensional model estimating section that estimates a three-dimensional model of the body tissues based on the two-dimensional image;
   a vector calculating section that detects one voxel group including the edge estimated as a part of the three-dimensional model and that calculates a normal vector and a reverse normal vector, which is a vector in which the direction of the normal vector is inverted 180 degrees, in voxels existing at predetermined intervals among the one voxel group;
   a raised shape determining section that detects a first voxel as a raise start position and a second voxel as a raise end position based on an intersection state of the normal vectors and an intersection state of the reverse normal vectors to thereby determine whether or not the body tissues estimated as the one voxel group are body tissues with a locally raised shape; and
   a lesion determining section that calculates a distance between the first voxel and the second voxel and determines that the body tissues estimated as the one voxel group are body tissues with a locally raised shape stemmed from a lesion if the distance is equal to or smaller than a predetermined distance.

4. The medical image processing apparatus according to claim 3, wherein
   the raised shape determining section sets as the first voxel, a first voxel where normal vectors within a predetermined size of vector start not to intersect each other and the number of intersections of reverse normal vectors within the predetermined size of vector becomes equal to or larger than a first threshold value.

5. The medical image processing apparatus according to claim 4, wherein
   the raised shape determining section sets as the second voxel, a first voxel where normal vectors within a predetermined size of vector start to intersect each other and the number of intersections of reverse normal vectors within the predetermined size of vector becomes smaller than a second threshold value.

6. The medical image processing apparatus according to claim 5, wherein
   the first threshold value is a value equal to the second threshold value.

7. A medical image processing method comprising:
   storing step of storing in an image storage a two-dimensional image of an image of body tissues inside a body cavity inputted from a medical image pickup apparatus;
   a three-dimensional model estimating step of estimating the three-dimensional model of body tissues based on the two-dimensional image of the image of the body tissues inside the body cavity inputted from the medical image pickup apparatus;
   a voxel detecting step of detecting one voxel existing on a nearest side in a view direction of the medical image pickup apparatus among voxels included in the three-dimensional model;
   a raised shape detecting step of acquiring one curved surface including the one voxel to detect a position with gradient variation on the one curved surface and to determine whether or not body tissues with a locally raised shape exist in the position in the three-dimensional model; and the raised shape detecting step is a step of tracing the one curved surface along a plurality of trace lines set parallel to a predetermined axial direction and then determining that the body tissues with a locally raised shape exist in one position when detecting that the number of trace lines with intensity gradient variation in the one position in the predetermined axial direction among the plurality of trace lines is equal to or larger than one and equal to or smaller than a predetermined threshold value.

8. The medical image processing method according to claim 7, wherein
   the predetermined axial direction is a central axis direction of a lumen inside the body cavity.

9. A medical image processing method comprising:
   storing step of storing in an image storage a two-dimensional image of an image of body tissues inside a body cavity inputted from a medical image pickup apparatus;
   an edge extracting step of extracting an edge of the two-dimensional image based on the inputted two-dimensional image of the image of the body tissues inside the body cavity;

a three-dimensional model estimating step of estimating a three-dimensional model of the body tissues based on the two-dimensional image;

a vector calculating step of detecting one voxel group including the edge estimated as a part of the three-dimensional model and calculating a normal vector and a reverse normal vector, which is a vector in which the direction of the normal vector is inverted 180°, in voxels existing at predetermined intervals among the one voxel group;

a raised shape determining step of detecting a first voxel as a raise start position and a second voxel as a raise end position based on an intersection state of the normal vectors and an intersection state of the reverse normal vector to thereby determine whether or not the body tissues estimated as the one voxel group are body tissues with a locally raised shape; and a lesion determining step of calculating a distance between the first voxel and the second voxel and determining that the body tissues estimated as the one voxel group are body tissues with a locally raised shape stemmed from a lesion if the distance is equal to or smaller than a predetermined distance.

10. The medical image processing method according to claim 9, wherein the raised shape determining step is a step of setting as the first voxel, a first voxel where normal vectors within a predetermined size of vector start not to intersect each other and the number of intersections of reverse normal vectors within the predetermined size of vector becomes equal to or larger than a first threshold value.

11. The medical image processing method according to claim 10, wherein the raised shape determining step is a step of setting as the second voxel, a first voxel where normal vectors within a predetermined size of vector start to intersect each other and the number of intersections of reverse normal vectors within the predetermined size of vector becomes smaller than a second threshold value.

12. The medical image processing method according to claim 11, wherein the first threshold value is a value equal to the second threshold value.

* * * * *